United States Patent [19]
Kelly

[11] Patent Number: 5,851,424
[45] Date of Patent: Dec. 22, 1998

[54] PHOTO CROSS-LINKABLE LIQUID CRYSTALLINE 1,4-DIOXANE-2,3 DIYL DERIVATIVES

[75] Inventor: Stephen Kelly, Beverley, England

[73] Assignee: Rolic AG, Zug, Switzerland

[21] Appl. No.: 686,974

[22] Filed: Jul. 25, 1996

[30] Foreign Application Priority Data

Jul. 28, 1995 [CH] Switzerland ............................ 2219/95
May 9, 1996 [EP] European Pat. Off. .............. 96107342

[51] Int. Cl.⁶ .......................... C09K 19/34; C09K 19/52; C07D 319/06; C07C 69/75
[52] U.S. Cl. ............................... 252/299.61; 252/299.62; 252/299.67; 252/299.01; 252/299.6; 549/369; 549/370; 546/339; 546/342; 568/647; 560/1; 560/60; 560/100; 560/65; 560/76; 560/102; 560/108; 544/298
[58] Field of Search ................ 252/299.61, 299.01, 252/299.6, 299.63, 299.67, 299.62; 549/369, 370; 560/1, 60, 100; 546/339, 342; 544/298

[56] References Cited

U.S. PATENT DOCUMENTS 3,291,624  12/1966  Jeffreys et al. ........................ 106/125
5,567,349  10/1996  Kelly et al. ........................ 252/299.01

FOREIGN PATENT DOCUMENTS 331233   9/1989   European Pat. Off. .
630 892  12/1994  European Pat. Off. .
2142020  1/1985   United Kingdom .
95/16007 6/1995   WIPO .

OTHER PUBLICATIONS

Derwent Abstract No. AN–95–216450, 1995.
Derwent Abstract No. AN–95–044859, 1994.

*Primary Examiner*—C. H. Kelly
*Attorney, Agent, or Firm*—Bryan Cave LLP

[57] ABSTRACT

The present invention is concerned with photo cross-linkable liquid crystalline compounds of the general formula

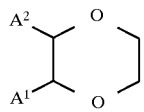

wherein $A^1$ and $A^2$ each represent a cross-linkable, mesogenic residue, liquid crystalline mixtures which contain such compounds and their use in the cross-linked state as optical components.

130 Claims, No Drawings

PHOTO CROSS-LINKABLE LIQUID CRYSTALLINE 1,4-DIOXANE-2,3 DIYL DERIVATIVES

BACKGROUND OF THE INVENTION

The present invention is concerned with photo cross-linkable liquid crystalline 1,4-dioxane-2,3-diyl derivatives, liquid crystalline mixtures which contain such compounds and their use in the cross-linked state for optical components.

Photo cross-linkable liquid crystals, which are provided with a suitable amount of a photo initiator, can be oriented on a substrate or in a cell by suitable orienting layers or in a field and can then in this state be cross-linked by irradiation with light of a suitable wavelength. The structure thereby produced remains even at high temperatures. Thus, optical components such as, for example, wave guides, optical grids and filters, piezoelectric cells and cells having non-linear optical (NLO) properties, etc., can be produced. Such optical components can be used, for example, for frequency doubling (SHG) or in color filters.

Further properties such as, for example, the birefringence, the refractive index, the transparency, etc. must fulfill different requirements depending on the field of use. Thus, materials for optical filters should have a strong absorption in a direction perpendicular to the filter surface.

In addition to the general use of photo cross-linkable liquid crystals for optical components, such liquid crystalline materials are suitable as a cladding for glass fibers for optical data transmission. The use of such materials increases the elastic modulus in the longitudinal axis of the fiber, reduces the thermal expansion coefficient and avoids microdistortion losses. This leads to an increased mechanical stability.

The photo cross-linkable liquid crystals must have a good chemical and thermal stability, good solubility in common solvents and a good stability towards electric fields and electromagnetic radiation. They should have a suitable mesophase in a temperature range of about 25° C. to about +100° C., especially of about 25° C. to about +80° C. Moreover, it is important that the components have a good miscibility with one another, since liquid crystals are usually used as mixtures of several components. Conventional photochemically oligomerisable or polymerisable liquid crystals usually have a high melting point and clearing point. This has the disadvantage that a spontaneous, thermal polymerization can occur prematurely during processing, which is carried out at temperatures barely below the clearing point, because at this temperature the viscosity in the liquid crystalline state is at the lowest and is therefore favorable for a good orientability. This spontaneous polymerization leads to the formation of domains, whereby the optical and thermal properties in the cross-linked layers which are produced can be clearly influenced. The melting point can be decreased by the production of complicated mixtures having several components, which permits a processing at lower temperatures, but brings with it the danger of a crystallization of the conventional polymerisable liquid crystals. Photochemically oligomerisable or polymerisable compounds are described, for example, in EP-A-0 331 233.

There is accordingly the need, especially for use in optical filters, to produce photochemically oligomerisable or polymerisable compounds which have relatively low melting points and clearing points in order that they can be processed very readily at temperatures above room temperature in the liquid crystalline state and also in solution. Further, they should be orientable and structurable as domain-free as possible and also should have an excellent thermal stability and long-term stability in the cross-linked state. Moreover, especially for optical retarders, mixtures having an adjustable optical isotropy should be available in order that, for example, the optical delay of an optical retarder can be adjusted. Conventional photochemically oligomerisable or polymerisable liquid crystals as described, for example, in EP-A-0 331 233 contain predominantly aromatic rings and therefore usually have a very large optical anisotropy.

SUMMARY OF THE INVENTION

The present invention now provides compounds which are suitable in an outstanding manner as single components or as components of such liquid crystal mixtures. These are compounds of the formula:

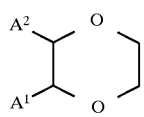
                                                              I wherein $A^1$ and $A^2$ each represent a cross-linkable, mesogenic residue.

DETAILED DESCRIPTION OF THE INVENTION

The present invention now provides compounds which are suitable in an outstanding manner as single components or as components of such liquid crystal mixtures. These are compounds of the formula:

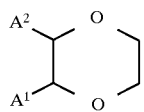
                                                              I wherein $A^1$ and $A^2$ each represent a cross-linkable, mesogenic residue.

Since the compounds of the invention or mixtures containing such compounds have a mesophase, they can also, prior to the cross-linking, be oriented by means known in the art on an orienting layer by the application of an electric or magnetic field. A uniform layer is produced in this manner.

Preferably, the mesogenic residues $A^1$ and $A^2$ each are a residue of the formula:

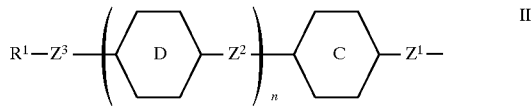
                                                              II wherein rings C and D each independently are pyridine-2,5-diyl, pyrimidine-2,5-diyl, trans-1,4-cyclohexylene, trans-1,3-dioxane-2,5-diyl or 1,4-phenylene unsubstituted or substituted with halogen, methyl or cyano;

$Z^1$ is —$CH_2$—$(CH_2)_m$—, —$(CH_2)_mO$—, —$O(CH_2)_m$—, —COO—, —OOC—, —$(CH_2)_mCOO$— or —$(CH_2)_mOOC$—;

$Z^2$ is a single bond, —$CH_2CH_2$—, —$CH_2O$—, —$OCH_2$—, —COO—, —OOC—, —$(CH_2)_4$—, —$O(CH_2)_3$— or —$(CH_2)_3O$—;

$Z^3$ is —$(CY_2)_m$—, —$O(CY_2)_m$—, —$(CY_2)_mO$—, —$(CY_2)_mCOO$—, —$(CY_2)_mOOC$—, —$(Si[(CH_3)_2]O)$ $_m$—, —OCH$_2$(Si[(CH$_3$)$_2$]O)$_m$Si[(CH$_3$)$_2$]CH$_2$O— or
—NHCH$_2$(Si[(CH$_3$)$_2$]O)$_m$Si[(CH$_3$)$_2$]CH$_2$NH—;

Y is hydrogen or fluorine;

n is 0, 1 or 2;

m is a whole number of 1 to 16; and

R$^1$ is a cross-linkable group of the structure CH$_2$=CH—, CH$_2$=CH—COO—, CH$_2$=C(CH$_3$)—COO—, CH$_2$=C(Cl)—COO—, CH$_2$=C(Ph)—COO—, CH$_2$=CH—COO—Ph—, CH$_2$=CH—CO—NH—, CH$_2$=C(CH$_3$)—CONH—, CH$_2$=C(Cl)—CONH—, CH$_2$=C(Ph)—CONH—, CH$_2$=C(COOR')—CH$_2$—COO—, CH$_2$=CH—O—, CH$_2$=CH—OOC—, Ph—CH=CH—, CH$_3$—C(=NR')—, cis,trans HOO—CR'=CR'—COO—,

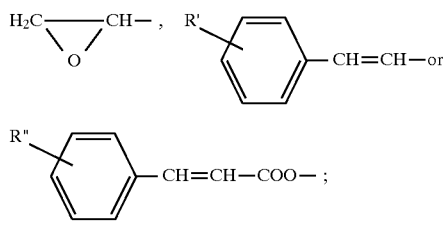

Ph is phenyl;

R' is lower alkyl; and

R" is methyl, methoxy, cyano or halogen;

with the proviso that R$^1$-Z$^3$ contains no —O—O— or —N—O— groups.

Compounds of the invention in which the two mesogenic residues A$^1$ and A$^2$ are the same are especially preferred.

Residues A$^1$ and A$^2$ of formula II in which rings C and D each independently are pyridine-2,5-diyl, pyrimidine-2,5-diyl or 1,4-phenylene which is unsubstituted or substituted with fluorine, Z$^1$ is —CH$_2$—CH$_2$—, —CH$_2$O—, —COO— or —OOC—, Z$^2$ is a single bond, —CH$_2$CH$_2$—, —CH$_2$O—, —OCH$_2$—, —COO— or —OOC— and Z$^3$ is —(CH$_2$)$_m$—, (CH$_2$)$_m$O—, —(CH$_2$)$_m$COO— or —(CH$_2$)$_m$OOC— are especially preferred.

The cross-linkable group R$^1$ preferably is CH$_2$=CH—COO—, CH$_2$=C(CH$_3$)—COO—, CH$_2$=C(Cl)—COO—, CH$_2$=C(Ph)—COO—, CH$_2$=CH—COO—Ph—CH$_2$=CH—CONH—, CH$_2$=C(CH$_3$)—CONH—, CH$_2$=C(Ph)—CONH—, CH$_2$=CH-O—, CH$_2$=CH—OOC—, cis,trans —HOO—CR'=CR'—COO—,

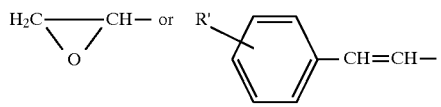

wherein R' has the significance given above.

It is these R$^1$ residues which can be cross-linked photochemically after orientation of the compounds of the invention in a field.

Especially preferred groups R$^1$ are CH$_2$=CH—COO—, CH$_2$=C(CH$_3$)—COO—, CH$_2$=CH—O— and

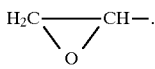

The terms used above will be explained hereinafter:

"1,4-phenylene optionally substituted with halogen, methyl and/or cyano" embraces in the present invention 1,4-phenylene and 1,4-phenylene mono- or multiply-substituted with fluorine, bromine, chlorine, methyl or cyano, such as, for example, 2- or 3-fluoro-1,4-phenylene, 2,3-difluoro- 1 ,4-phenylene, 2,6- or 3,5-difluoro-1,4-phenylene, 2- or 3-chloro- 1 ,4-phenylene, 2,3-dichloro-1, 4-phenylene, 2,6- or 3,5-dichloro-1,4-phenylene, 2- or 3-bromo-1,4-phenylene, 2- or 3-methyl-1,4-phenylene, 2- or 3-cyano-1,4-phenylene and the like;

"Lower alkyl" embraces straight-chain or branched residues with 1 to 5 carbon atoms such as methyl, ethyl, propyl, butyl, pentyl, iso-propyl, iso-butyl, t.butyl and the like;

"halogen" stands for fluorine, chlorine or bromine, especially for fluorine.

The mesophase type of the compounds in accordance with the invention can be influenced by varying the rings in the side-chains A$^1$ and A$^2$. Thus, aromatic rings such as phenylene have the tendency to produce smectic phases, while saturated rings such as trans-1,4-cyclohexylene or trans-1, 3-dioxane-2,5-diyl rings promote nematic tendencies.

Preferably, the mesogenic residues A$^1$ and A$^2$ are a residue of formula II in which n=1, i.e., a residue of formula II-a

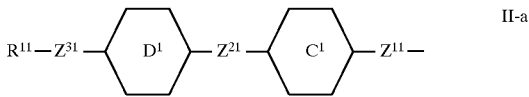

wherein rings C$^1$ and D$^1$ are pyridine-2,5-diyl, pyrimidine-2,5-diyl or 1,4-phenylene optionally substituted with fluorine;

Z$^{11}$ is —CH$_2$CH$_2$—, —CH$_2$O—, —COO— or —OOC—;

Z$^{21}$ is a single bond, —CH$_2$O—, —COO— or —OOC—;

Z$^{31}$ is —(CH$_2$)$_{m'}$—, —(CH$_2$)$_{m'}$O—, —(CH$_2$)$_{m'}$COO— or —(CH$_2$)$_{m'}$OOC—;

m' is a whole number of 3 to 12; and

R$^{11}$ is CH$_2$=CH—COO—, CH$_2$=C(CH$_3$)—COO—, CH$_2$=CH—O— or

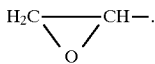

Compounds of the following formulae are particularly preferred:

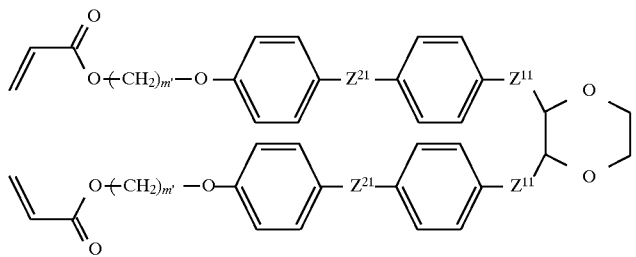

I-A

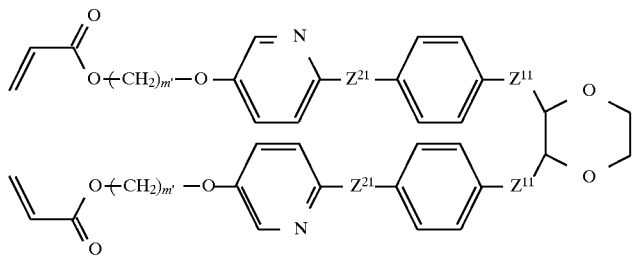

I-B and

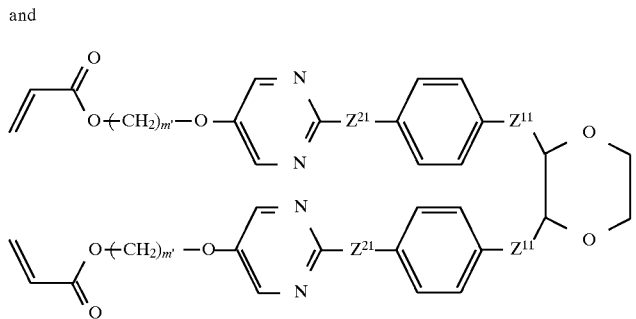

I-C wherein $Z^{11}$ is —COO—;

$Z^{21}$ is a single bond or —COO—, especially —COO—; and m' is an integer from 3 to 12.

The compounds of the invention in which $A^1$ and $A^2$ are the same are very readily accessible synthetically and can be produced, for example, analogously to the methods illustrated in Schemes 1 to 5. Thus, trans-2,3-dihydroxy-1,4-dioxane can be reacted with (ω-acryloyloxyalkyloxy)-substituted carboxylic acids in a manner known per se. This esterification can be effected, for example, via the corresponding methylsulphonate in tetrahydrofuran or in the presence of N,N'-dicyclohexylcarbodiimide and 4-(dimethylamino)pyridine in dichloromethane or another suitable solvent such as, e.g., chloroform. Trans-2,3-dihydroxy-1,4-dioxane can also be reacted in a Williamson etherification with (ω-acryloyloxyalkyloxy)-substituted benzyl tosylates. This esterification can be effected, for example, at room temperature in the presence of potassium tert.-butylate in dimethoxyethane or another suitable solvent such as e.g. N,N'-dimethylformamide. Trans-2,3-dihydroxy-1,4-dioxane is commercially available.

Compounds of the invention in which $A^1$ and $A^2$ are different can be produced by mono-esterifying trans-2,3-dihydroxy-1,4-dioxane with an (ω-acryloyloxyalkyloxy)-substituted carboxylic acid. Subsequent esterification with a different (ω-acryloyloxyalkyloxy)-substituted carboxylic acid gives the asymmetric diester. The corresponding asymmetric diethers are accessible by an analogous two-step process in which, for example, trans-2,3-dihydroxy-1,4-dioxane is firstly monoalkylated with an (ω-acryloyloxyalkyloxy)-substituted benzyl tosylate and subsequently with a different (ω-acryloyloxyalkyloxy)-substituted benzyl tosylate. The starting materials are known and are in part commercially available.

The reactions illustrated in Schemes 1 to 5 are standard methods in liquid crystal chemistry. The symbols used therein have the aforementioned significances.

Scheme 1
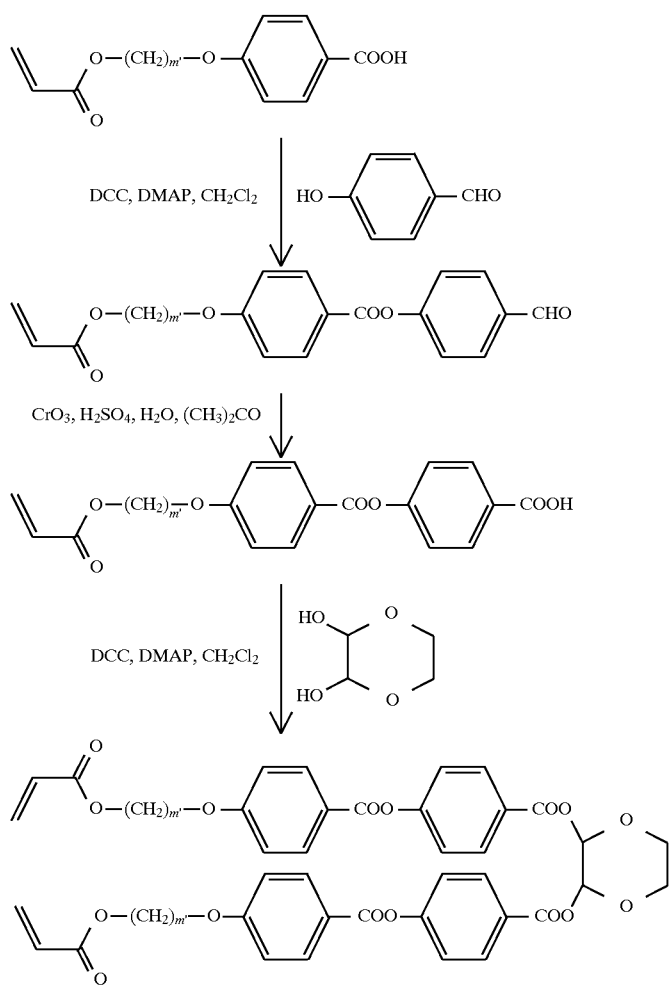
Scheme 2
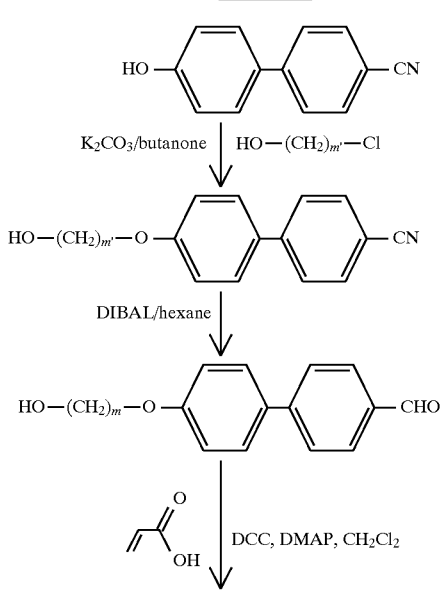
-continued
Scheme 2
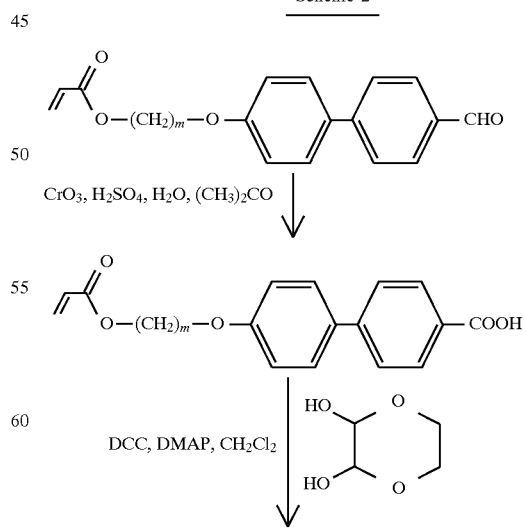

-continued
Scheme 2
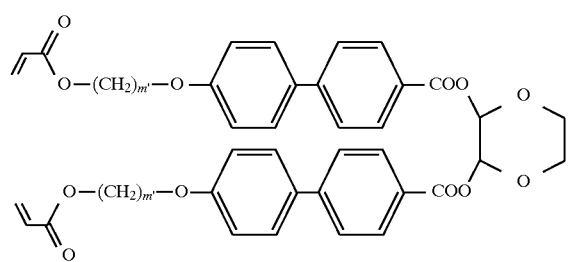
-continued
Scheme 3
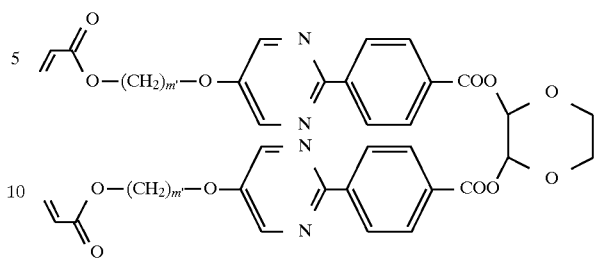
Scheme 3
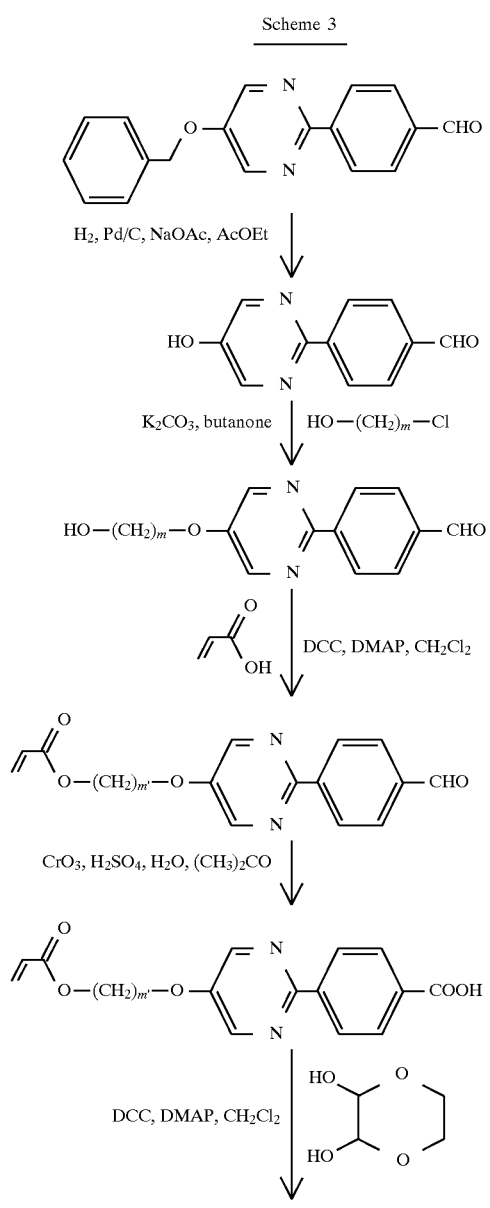
Scheme 4
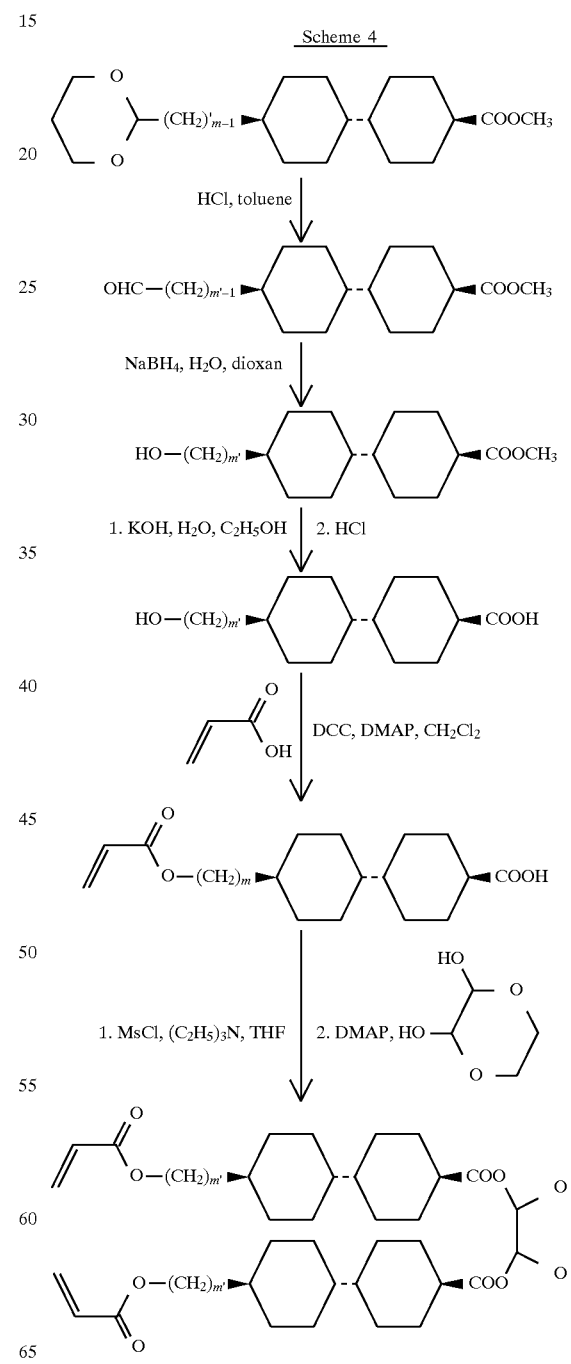

Scheme 5

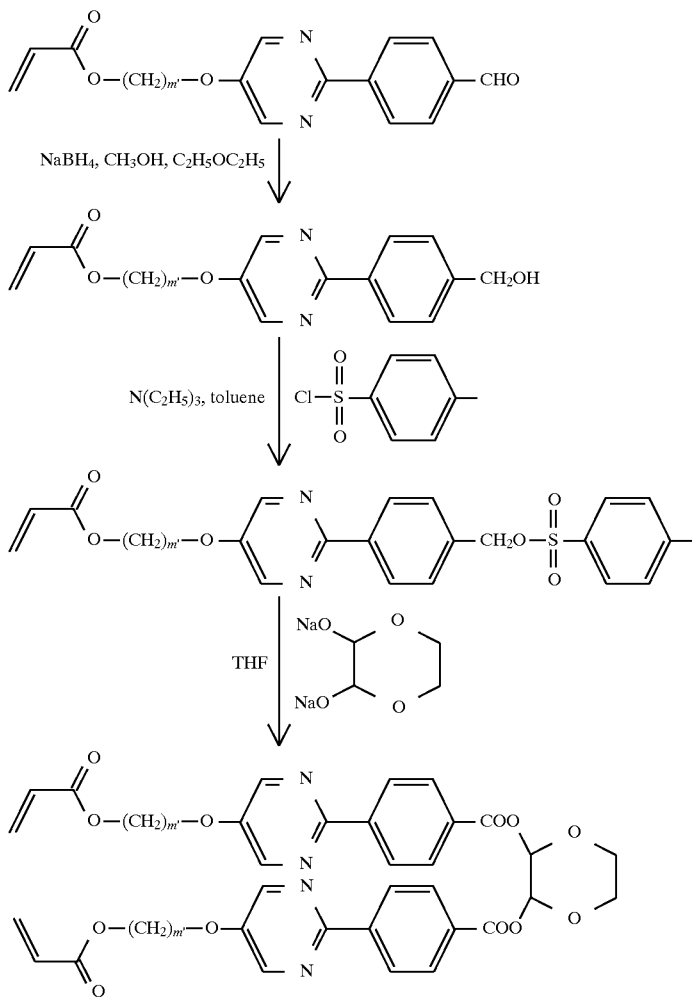

A small amount of BHT (2,6-di-tert.-butyl-4-methyl-phenol/"butylhydroxytoluene") is admixed in each step in order to stop undesired thermal cross-linkage.

The compounds of the invention can be used as single compounds or in the form of mixtures with one another and/or with other liquid crystal components.

The liquid crystalline mixtures in accordance with the invention contain at least 2 components, of which at least one component is a compound of the invention. A second component and any other components can be additional compounds of the invention or other known liquid crystalline compounds having a photo cross-linkable group. One or more chiral components can also be present in the mixture.

Having regard to the good solubility of the compounds of the invention and having regard to their good miscibility with one another, the content of compounds of the invention in the mixtures in accordance with the invention can be high and can amount to 100 wt. %.

The mixtures in accordance with the invention preferably contain, in addition to one or more compounds of the invention, one or more compounds from the group of compounds of the formulae:

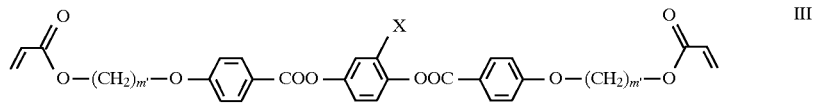

-continued
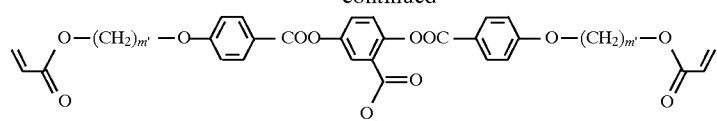           IV
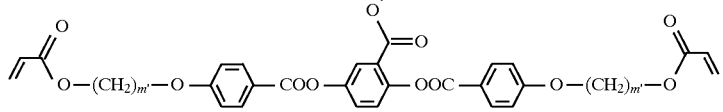           V
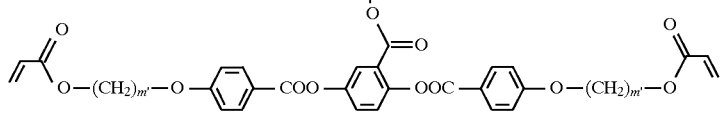           VI
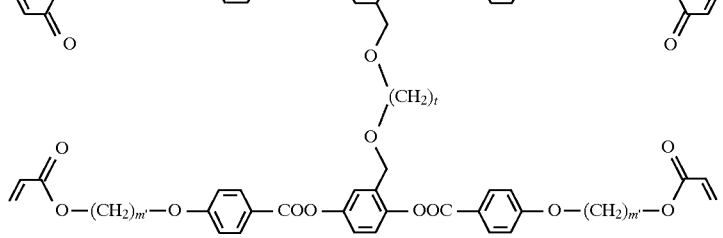           VII
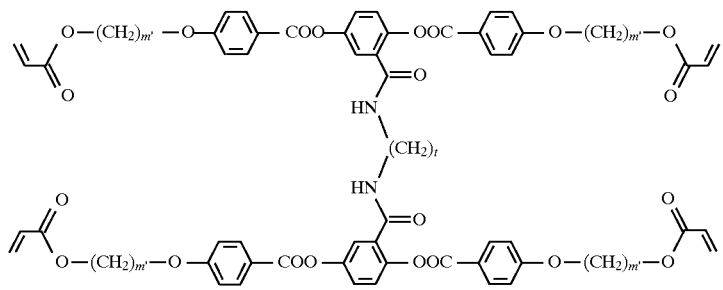           VIII
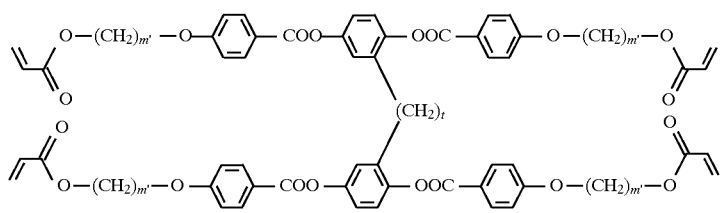
           IX

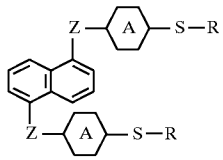

-continued

X wherein
X is hydrogen, fluorine, chlorine, bromine or methyl;
m' is an integer from 3 to 12;
t is an integer from 2 to 12;
Z is —OCH$_2$— or —OOC—;
A is 1,4-phenylene or 2- or 3-fluoro-1,4-phenylene;
S is —(CH$_2$)$_m{}'$— or —(CH$_2$)$_m{}'$O—; and
R is CH$_2$=CH—COO—, CH$_2$=C(CH$_3$)—COO—, CH$_2$=CH—O— or

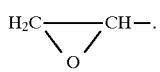

The production of the compounds of the invention and of liquid crystalline mixtures containing these compounds is illustrated in more detail by the following Examples.

EXAMPLE 1

0.43 g of N,N'-dicyclohexylcarbodiimide was added within 5 minutes while stirring to a solution of 0.1 g of trans-2,3-dihydroxy-1,4-dioxane, 0.9 g of 4-(4-[8-acryloyloxyoctyloxy]-phenylcarbonyloxy)benzoic acid and 0.05 g of 4-(dimethylamino)-pyridine in 25 ml of dichloromethane. The reaction mixture was stirred overnight, filtered and the filtrate was concentrated. Chromatography of the residue on silica gel with hexane/ethyl acetate (vol. 8:2) and recrystallization from ethyl alcohol of the fractions which were pure according to thin-layer chromatography gave 0.15 g of trans-2,3-bis[4-(4-[8-acryloxyoctyloxy]phenylcarbonyloxy)phenylcarbonyloxy]-1,4-dioxane; m.p. (C—N) 98° C. and cl.p. (N—I) 153° C.

The following compounds can be prepared in an analogous manner:

trans-2,3-Bis[4-(4-[3-acryloyloxypropyloxy]phenyl-carbonyloxy)phenylcarbonyloxy]-1,4-dioxane;
trans-2,3-bis[4-(4-[4-acryloyloxybutoxy]phenyl-carbonyloxy)-phenylcarbonyloxy]-1,4-dioxane;
trans-2,3-bis[4-(4-[5-acryloyloxypentyloxy]phenyl-carbonyloxy)phenylcarbonyloxy]-1,4-dioxane;
trans-2,3-bis [4-(4-[6-acryloyloxyhexyloxy]phenyl-carbonyloxy)phenylcarbonyloxy]-1,4-dioxane;
trans-2,3-bis[4-(4-[7-acryloyloxyheptyloxy]phenyl-carbonyloxy)phenylcarbonyloxy]-1,4-dioxane;
trans-2,3-bis[4-(4-[9-acryloyloxynonyloxy]phenyl-carbonyloxy)phenylcarbonyloxy]-1,4-dioxane;
trans-2,3-bis[4-(4-[10-acryloyloxydecyloxy]phenyl-carbonyloxy)phenylcarbonyloxy]-1,4-dioxane;
trans-2,3-bis[4-(4-[11-acryloyloxyundecyloxy]phenyl-carbonyloxy)phenylcarbonyloxy]-1,4-dioxane;
trans-2,3-bis[4-(4-[12-acryloyloxydodecyloxy]phenyl-carbonyloxy)phenylcarbonyloxy]-1,4-dioxane;
trans-2,3-bis(4-[3-acryloyloxypropyloxy]biphenyl-4'-carbonyloxy)-1,4-dioxane;
trans-2,3-bis(4-[4-acryloyloxybutoxy]biphenyl-4'-carbonyloxy)-1,4-dioxane;
trans-2,3-bis(4-[5-acryloyloxypentyloxy]biphenyl-4'-carbonyloxy)-1 ,4-dioxane;
trans-2,3-bis(4-[6-acryloyloxyhexyloxy]biphenyl-4'-carbonyloxy)-1,4-dioxane;
trans-2,3-bis(4-[7-acryloyloxyheptyloxy]biphenyl-4'-carbonyloxy)-1,4-dioxane;
trans-2,3-bis(4-[8-acryloyloxyoctyloxy]biphenyl-4'-carbonyloxy)-1,4-dioxane;
trans-2,3-bis(4-[9-acryloyloxynonyloxy]biphenyl-4'-carbonyloxy)-1,4-dioxane;
trans-2,3-bis(4-[10-acryloyloxydecyloxy]biphenyl-4'-carbonyloxy)-1,4-dioxane;
trans-2,3-bis(4-[11-acryloyloxyundecyloxy]biphenyl-4'-carbonyloxy)-1,4-dioxane;
trans-2,3-bis(4-[12-acryloyloxydodecyloxy]biphenyl-4'-carbonyloxy)-1,4-dioxane;
trans-2,3-bis[4-(5-[3-acryloyloxypropyloxy]pyrimidin-2-yl)phenylcarbonyloxy]- 1,4-dioxane;
trans-2,3-bis[4-(5-[4-acryloyloxybutyloxy]pyrimidin-2-yl)phenylcarbonyloxy]- 1,4-dioxane;
trans-2,3-bis[4-(5-[5-acryloyloxypentyloxy]pyrimidin-2-yl)phenylcarbonyloxy]-1,4-dioxane;
trans-2,3-bis[4-(5-[6-acryloyloxyhexyloxy]pyrimidin-2-yl)phenylcarbonyloxy]-1,4-dioxane;
trans-2,3-bis[4-(5-[7-acryloyloxyheptyloxy]pyrimidin-2-yl)phenylcarbonyloxy]-1,4-dioxane;
trans-2,3-bis[4-(5-[8-acryloyloxyoctyloxy]pyrimidin-2-yl)phenylcarbonyloxy]-1,4-dioxane;
trans-2,3-bis[4-(5-[9-acryloyloxynonyloxy]pyrimidin-2-yl)phenylcarbonyloxy]-1 ,4-dioxane;
trans-2,3-bis[4-(5-[10-acryloyloxydecyloxy]pyrimidin-2-yl)phenylcarbonyloxy]-1,4-dioxane;
trans-2,3-bis[4-(5-[ 1 1-acryloyloxyundecyloxy]pyrimidin-2-yl)phenylcarbonyloxy]-1,4-dioxane;
trans-2,3-bis[4-(5-[12-acryloyloxydodecyloxy]pyrimidin-2-yl)phenylcarbonyloxy]-1,4-dioxane;
trans-2,3-bis[4-(5-[3-acryloyloxypropyloxy]pyridin-2-yl)phenylcarbonyloxy]-1,4-dioxane;
trans-2,3-bis[4-(5-[4-acryloyloxybutyloxy]pyridin-2-yl)phenylcarbonyloxy]-1 ,4-dioxane;
trans-2,3-bis[4-(5-[5-acryloyloxypentyloxy]pyridin-2-yl)phenylcarbonyloxy]-1,4-dioxane;
trans-2,3-bis[4-(5-[6-acryloyloxyhexyloxy]pyridin-2-yl)phenylcarbonyloxy]-1,4-dioxane;
trans-2,3-bis[4-(5-[7-acryloyloxyheptyloxy]pyridin-2-yl)phenylcarbonyloxy]-1,4-dioxane;
trans-2,3-bis[4-(5-[8-acryloyloxyoctyloxy]pyridin-2-yl)phenylcarbonyloxy]-1,4-dioxane;
trans-2,3-bis[4-(5-[9-acryloyloxynonyloxy]pyridin-2-yl)phenylcarbonyloxy]-1,4-dioxane;
trans-2,3-bis[4-(5-[10-acryloyloxydecyloxy]pyridin-2-yl)phenylcarbonyloxy]-1,4-dioxane;
trans-2,3-bis[4-(5-[11-acryloyloxyundecyloxy]pyridin-2-yl)phenylcarbonyloxy]-1,4-dioxane;
trans-2,3-bis[4-(5-[12-acryloyloxydodecyloxy]pyridin-2-yl)phenylcarbonyloxy]-1,4-dioxane;
trans-2,3-bis[2-(4-[8-acryloyloxyoctyloxy]phenyl)pyrimidin-5-ylcarbonyloxy]-1,4-dioxane;
trans-2,3-bis[2-(4-[8-acryloyloxyoctyloxy]phenyl)pyridin-5-ylcarbonyloxy]-1,4-dioxane;
trans-2,3-bis[trans-4-(trans-4-[3-acryloyloxypropyl]-cyclohexyl)cyclohexancarbonyloxy]-1,4-dioxane;

trans-2,3-bis[trans-4-(2-[trans-4-(3-acryloyloxypropyl)-cyclohexyl]ethyl)cyclohexancarbonyloxy]-1,4-dioxane;
trans-2,3-bis[4-(trans-4-[3-acryloyloxypropyl]cyclohexyl)-phenylcarbonyloxy]-1,4-dioxane;
trans-2,3-bis [4-(2-[trans-4-(3-acryloyloxypropyl)cyclohexyl]ethyl)-phenylcarbonyloxy]-1,4-dioxane.

EXAMPLE 2

A solution of 0.2 g of trans-2,3-dihydroxy-1,4-dioxane, 0.5 g of sodium hydride and 50 ml of tetrahydrofuran is stirred for 7 hours. 1.1 g of 4-(5-[8-acryloyloxyoctyloxy]pyrimidin-2-yl)benzyl tosylate are added and the mixture is stirred at room temperature overnight, poured into 100 ml of water and then extracted three times with 50 ml of diethyl ether each time. The organic phases are combined, washed twice with 100 ml of water each time, dried over magnesium sulphate, filtered and the filtrate is concentrated. Chromatographic purification of the residue on silica gel with cyclohexane/ethyl acetate (vol. 8:2) and two-fold recrystallization from a cyclohexane/ethyl acetate mixture (vol. 8:2) of the fractions which are pure according to thin-layer chromatography gives 1.1 g of trans-2,3-bis[4-(5-[8-acryloyloxyoctyloxy]pyrimidin-2-yl)benzyloxy]-1,4-dioxane.

The following compounds can be prepared in an analogous manner:
trans-2,3-Bis[4-(4-[3-acryloyloxypropyloxy]phenyl-carbonyloxy)benzyloxy]-1,4-dioxane;
trans-2,3-bis [4-(4-[4-acryloyloxybutoxy]phenyl-carbonyloxy)benzyloxy]-1,4-dioxane;
trans-2,3-bis[4-(4-[5-acryloyloxypentyloxy]phenyl-carbonyloxy)benzyloxy]-1,4-dioxane;
trans-2,3-bis[4-(4-[6-acryloyloxyhexyloxy]phenyl-carbonyloxy)benzyloxy]-1,4-dioxane;
trans-2,3-bis[4-(4-[7-acryloyloxyheptyloxy]phenyl-carbonyloxy)benzyloxy]-1,4-dioxane;
trans-2,3-bis[4-(4-[9-acryloyloxynonyloxy]phenyl-carbonyloxy)benzyloxy]-1,4-dioxane;
trans-2,3-bis [4-(4-[10-acryloyloxydecyloxy]phenyl-carbonyloxy)benzyloxy]-1,4-dioxane;
trans-2,3-bis[4-(4-[11-acryloyloxyundecyloxy]phenyl-carbonyloxy)benzyloxy]-1,4-dioxane;
trans-2,3-bis[4-(4-[12-acryloyloxydodecyloxy]phenyl-carbonyloxy)benzyloxy]-1,4-dioxane;
trans-2,3-bis(4-[3-acryloyloxypropyloxy]biphenyl-4'-methoxy)-1,4-dioxane;
trans-2,3-bis(4-[4-acryloyloxybutoxy]biphenyl-4'-methoxy)-1,4-dioxane;
trans-2,3-bis(4-[5-acryloyloxypentyloxy]biphenyl-4'-methoxy)-1,4-dioxane;
trans-2,3-bis(4-[6-acryloyloxyhexyloxy]biphenyl-4'-methoxy)-1,4-dioxane;
trans-2,3-bis(4-[7-acryloyloxyheptyloxy]biphenyl-4'-methoxy)-1,4-dioxane;
trans-2,3-bis(4-[8-acryloyloxyoctyloxy]biphenyl-4'-methoxy)-1,4-dioxane;
trans-2,3-bis(4-[9-acryloyloxynonyloxy]biphenyl-4'-methoxy)-1,4-dioxane;
trans-2,3-bis(4-[10-acryloyloxydecyloxy]biphenyl-4'-methoxy)-1,4-dioxane;
trans-2,3-bis(4-[11-acryloyloxyundecyloxy]biphenyl-4'-methoxy)-1,4-dioxane;
trans-2,3-bis(4-[12-acryloyloxydodecyloxy]biphenyl-4'-methoxy)-1,4-dioxane;
trans-2,3-bis[4-(5-[3-acryloyloxypropyloxy]pyrimidin-2-yl)benzyloxy]-1,4-dioxane;
trans-2,3-bis[4-(5-[4-acryloyloxybutyloxy]pyrimidin-2-yl)benzyloxy]-1,4-dioxane;
trans-2,3-bis[4-(5-[5-acryloyloxypentyloxy]pyrimidin-2-yl)benzyloxy]-1,4-dioxane;
trans-2,3-bis[4-(5-[6-acryloyloxyhexyloxy]pyrimidin-2-yl)benzyloxy]-1,4-dioxane;
trans-2,3-bis[4-(5-[7-acryloyloxyheptyloxy]pyrimidin-2-yl)benzyloxy]-1,4-dioxane;
trans-2,3-bis[4-(5-[8-acryloyloxyoctyloxy]pyrimidin-2-yl)benzyloxy]-1,4-dioxane;
trans-2,3-bis[4-(5-[9-acryloyloxynonyloxy]pyrimidin-2-yl)benzyloxy]-1,4-dioxane;
trans-2,3-bis[4-(5-[10-acryloyloxydecyloxy]pyrimidin-2-yl)benzyloxy]-1,4-dioxane;
trans-2,3-bis[4-(5-[11-acryloyloxyundecyloxy]pyrimidin-2-yl)benzyloxy]-1,4-dioxane;
trans-2,3-bis[4-(5-[12-acryloyloxydodecyloxy]pyrimidin-2-yl)benzyloxy]-1,4-dioxane;
trans-2,3-bis[4-(5-[3-acryloyloxypropyloxy]pyridin-2-yl)benzyloxy]-1,4-dioxane;
trans-2,3-bis[4-(5-[4-acryloyloxybutyloxy]pyridin-2-yl)benzyloxy]-1,4-dioxane;
trans-2,3-bis[4-(5-[5-acryloyloxypentyloxy]pyridin-2-yl)benzyloxy]-1,4-dioxane;
trans-2,3-bis[4-(5-[6-acryloyloxyhexyloxy]pyridin-2-yl)benzyloxy]-1,4-dioxane;
trans-2,3-bis[4-(5-[7-acryloyloxyheptyloxy]pyridin-2-yl)benzyloxy]-1,4-dioxane;
trans-2,3-bis[4-(5-[8-acryloyloxyoctyloxy]pyridin-2-yl)benzyloxy]-1,4-dioxane;
trans-2,3-bis[4-(5-[9-acryloyloxynonyloxy]pyridin-2-yl)benzyloxy]- 1,4-dioxane;
trans-2,3-bis[4-(5-[10-acryloyloxydecyloxy]pyridin-2-yl)benzyloxy]-1,4-dioxane;
trans-2,3-bis[4-(5-[11-acryloyloxyundecyloxy]pyridin-2-yl)benzyloxy]-1,4-dioxane;
trans-2,3-bis[4-(5-[12-acryloyloxydodecyloxy]pyridin-2-yl)benzyloxy]-1,4-dioxane;
trans-2,3-bis[4-(5-[8-acryloyloxyoctyloxy]pyridin-2-yl)benzyloxy]-1,4-dioxane;
trans-2,3-bis[(2-[4-(8-acryloyloxyoctyloxy)phenyl]pyrimidin-5-yl)methoxy]-1,4-dioxane;
trans-2,3-bis[(trans-4-(trans-4-[3-acryloyloxypropyl]-cyclohexyl)cyclohexyl)methoxy]-1,4-dioxane;
trans-2,3-bis[(trans-4-[2-(trans-4-[3-acryloyloxypropyl]-cyclohexyl)ethyl]cyclohexyl)methoxy]-1,4-dioxane;
trans-2,3-bis[4-(trans-4-[3-acryloyloxypropyl]cyclohexyl)-benzyloxy]-1,4-dioxane;
trans-2,3-bis[4-(2-[trans-4-(3-acryloyloxypropyl)-cyclohexyl]ethyl)benzyloxy]-1,4-dioxane.

I claim:

1. A compound having the formula:

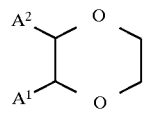   I wherein $A^1$ and $A^2$ are residues of formula:

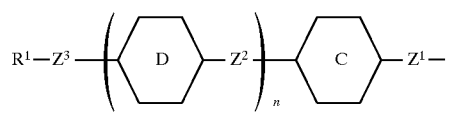   II wherein
rings C and D each independently are pyridine-2,5 diyl, pyrimidine-2,5-diyl, trans-1,4-cyclohexylene, trans-1,3-dioxane-2,5-diyl or 1,4 phenylene unsubstituted or substituted with halogen, methyl or cyano;

$Z^1$ is —$CH_2$—$(CH_2)_m$—, —$(CH_2)_mO$—, —$O(CH_2)_m$—, —COO—, —OOC—, —$(CH_2)_m$COO— or —$(CH_2)_m$OOC—;

$Z^2$ is a single bond —$CH_2CH_2$—, —$CH_2O$—, —$OCH_2$—, —COO—, —OOC—, —$(CH_2)_4$—, —$O(CH_2)_3$ or —$(CH_2)_3O$—;

$Z^3$ is —$(CY_2)_m$—, —$O(CY_2)_m$—, —$(CY_2)_mO$—, —$(CY_2)_mCOO$—, —$(CY_2)_mOOC$—, —$(Si[(CH_3)_2]O)_m$—, —$OCH_2(Si[(CH_3)_2]O)_mSi[(CH_3)_2]CH_2O$— or —$NHCH_2(Si[(CH_3)_2]O)_mSi[(CH_3)_2]CH_2NH$—;

Y is hydrogen or fluorine;

n is 0, 1 or 2;

m is an integer from 1 to 16; and $R^1$ is $CH_2$=CH—, $CH_2$=CH—COO—, $CH_2$=C($CH_3$)—COO—, $CH_2$=C(Cl)—COO—, $CH_2$=C(Ph)—COO—, $CH_2$=CH—COO—Ph—, $CH_2$=CH—CO—NH—, $CH_2$=C($CH_3$)—CONH—, $CH_2$=C(Cl)—CONH—, $CH_2$=C(Ph)—CONH—, $CH_2$=C(COOR')—$CH_2$—COO—, $CH_2$=CH—O—, $CH_2$=CH—OOC—, Ph—CH=CH—, $CH_3$—C(=NR')—, cis, trans HOO—CR'=CR'—COO—,

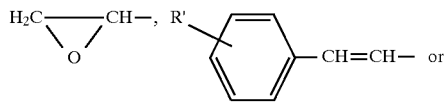

Ph is phenyl;

R' is lower alkyl; and

R" is methyl, methoxy, cyano or halogen;

with the proviso that $R^1$-$Z^3$ contains no —O—O— or —N—O— groups.

2. The compound of claim 1 wherein:

$Z^1$ is —$CH_2CH_2$—, —$CH_2O$, —COO—, —OOC—, —$(CH_2)_4$— or —$(CH_2)_3O$—; and n is 0 or 1.

3. The compound of claim 2 wherein:

C and D are independently pyridine-2,5-diyl, pyrimidine-2,5-diyl or 1,4-phenylene which is unsubstituted or substituted with fluorine, $Z^1$ is —$CH_2$—$CH_2$—, —$CH_2O$—, —COO— or —OOC—, $Z^2$ is a single bond, —$CH_2CH_2$—, —$CH_2O$—, —$OCH_2$—, —COO— or —OOC—, $Z^3$ is —$(CH_2)_m$—, —$(CH_2)_mO$—, —$(CH_2)_mCOO$— or —$(CH_2)_mOOC$, and $R^1$ is $CH_2$=CH—COO—, $CH_2$=C($CH_3$)—COO—, $CH_2$=C(Cl)—COO—, $CH_2$=C(Ph)—COO—, $CH_2$=CH—COO—Ph—, $CH_2$=CH—CONH—, $CH_2$=C($CH_3$)—CONH—, $CH_2$=C(Ph)—CONH—, $CH_2$=CH—O—, $CH_2$=CH—OOC—, cis,trans —HOO—CR'=CR'—COO—,

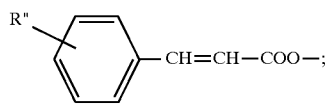

wherein R' is as in claim 2.

4. The compound of claim 3 wherein $A^1$ and $A^2$ are the same.

5. The compound of claim 4 wherein D is trans-1,4-cyclohexylene.

6. The compound of claim 5 wherein $R^1$ is $CH_2$=C($CH_3$)—COO—, $CH_2$=CH—O— or

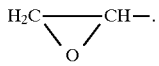

7. The compound of claim 6 wherein $Z^3$ is —$(CH_2)_3O$—, $R^1$ is $CH_2$=CH—COO— and n=1.

8. The compound of claim 7 wherein $Z^1$ is —COO—.

9. The compound of claim 8 wherein $Z^2$ is a single bond or —$CH_2$—$CH_2$— and C is trans-1,4-cyclohexylene or 1,4-phenylene.

10. The compound of claim 9 wherein said compound is trans-2,3-bis[trans-4-(trans-4-[3-acryloyloxypropyl]cyclohexyl)-cyclohexancarbonyloxy]-1,4-dioxane.

11. The compound of claim 10 wherein said compound is trans-2,3-bis[trans-4-(2-[trans-4-(3-acryloyloxypropyl)cyclohexyl]-ethyl)cyclohexancarbonyloxy]-1,4-dioxane.

12. The compound of claim 9 wherein said compound is trans-2,3-bis[4-(trans-4-[3-acryloyloxypropyl]cyclohexyl)phenyl-carbonyloxy]-1,4-dioxane.

13. The compound of claim 9 wherein said compound is trans-2,3-bis[4-(2-[trans-4-(3-acryloyloxypropyl)cyclohexyl]ethyl)-phenylcarbonyloxy]-1,4-dioxane.

14. The compound of claim 7 wherein $Z^1$ is —$CH_2O$—.

15. The compound of claim 14 wherein $Z^2$ is a single bond or —$CH_2$—$CH_2$— and C is trans-1,4-cyclohexylene or 1,4-phenylene.

16. The compound of claim 15 wherein said compound is trans-2,3-bis[(trans-4-(trans-4-[3-acryloyloxypropyl]-cyclohexyl)cyclohexyl)methoxy]-1,4-dioxane.

17. The compound of claim 15 wherein said compound is trans-2,3-bis[(trans-4-[2-(trans-4-[3-acryloyloxypropyl]cyclohexyl)-ethyl]cyclohexyl)methoxy]- 1,4-dioxane.

18. The compound of claim 15 wherein said compound is trans-2,3-bis[4-(trans-4-[3-acryloyloxypropyl]cyclohexyl)-benzyloxy]-1,4-dioxane.

19. The compound of claim 15 wherein said compound is trans-2,3-bis[4-(2-[trans-4-(3-acryloyloxypropyl)cyclohexyl]ethyl)-benzyloxy]-1,4-dioxane.

20. The compound of claim 4 wherein $A^1$ and $A^2$ are of the formula:

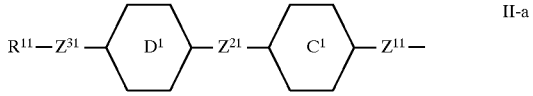

wherein $C^1$ and $D^1$ are pyridine-2,5-diyl, pyrimidine-2,5-diyl or 1,4-phenylene optionally substituted with fluorine;

$Z^{11}$ is —$CH_2CH_2$—, —$CH_2O$—, —COO— or —OOC—;

$Z^{21}$ is a single bond, —$CH_2O$—, —COO—, —OOC—;

$Z^{31}$ is —$(CH_2)_{m'}$—, —$(CH_2)_mO$—, —$(CH_2)_mCOO$— or —$(CH_2)_{m'}OOC$—;

m' is an integer from 3 to 12; and $R^{11}$ is $CH_2$=CH—COO—, $CH_2$=C($CH_3$)—COO—, $CH_2$=CH—O— or

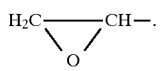

21. The compound of claim 20 wherein $Z^{11}$ is —COO—.
22. The compound of claim 21 wherein $Z^{21}$ is a single bond.
23. The compound of claim 22 wherein $D^1$ is 1,4-phenylene.
24. The compound of claim 23 wherein $C^1$ is pyridine-2,5-diyl, pyrimidine-2,5-diyl or 1,4-phenylene.
25. The compound of claim 24 wherein said compound is trans-2,3-bis[2-(4-[8-acryloyloxyoctyloxy]phenyl)pyrimidin-5-ylcarbonyloxy]-1,4-dioxane.
26. The compound of claim 24 wherein said compound is trans-2,3-bis[2-(4-[8-acryloyloxyoctyloxy]phenyl)pyridin-5-ylcarbonyloxy]-1,4-dioxane.
27. The compound of claim 20 wherein $Z^{11}$ is —CH$_2$O—.
28. The compound of claim 27 wherein $Z^{21}$ is a single bond.
29. The compound of claim 28 wherein $C^1$ and $D^1$ are pyridine-2,5-diyl, pyrimidine-2,5-diyl or 1,4-phenylene.
30. The compound of claim 29 wherein $C^1$ is 1,4-phenylene.
31. The compound of claim 30 wherein $D^1$ is pyrimidine-2,5-diyl.
32. The compound of claim 31 wherein said compound is trans-2,3-bis[4-(5-[8-acryloyloxyoctyloxy]pyrimidin-2-yl)benzyloxy]-1,4-dioxane.
33. The compound of claim 31 wherein said compound is trans-2,3-bis[4-(5-[3-acryloyloxypropyloxy]pyrimidin-2-yl)benzyloxy]-1,4-dioxane.
34. The compound of claim 31 wherein said compound is trans-2,3-bis[4-(5-[4-acryloyloxybutyloxy]pyrimidin-2-yl)benzyloxy]-1,4-dioxane.
35. The compound of claim 31 wherein said compound is trans-2,3-bis[4-(5-[5-acryloyloxypentyloxy]pyrimidin-2-yl)benzyloxy]-1,4-dioxane.
36. The compound of claim 31 wherein said compound is trans-2,3-bis[4-(5-[6-acryloyloxyhexyloxy]pyrimidin-2-yl)benzyloxy]-1,4-dioxane.
37. The compound of claim 31 wherein said compound is trans-2,3-bis[4-(5-[7-acryloyloxyheptyloxy]pyrimidin-2-yl)benzyloxy]-1,4-dioxane.
38. The compound of claim 31 wherein said compound is trans-2,3-bis[4-(5-[8-acryloyloxyoctyloxy]pyrimidin-2-yl)benzyloxy]-1,4-dioxane.
39. The compound of claim 31 wherein said compound is trans-2,3-bis[4-(5-[9-acryloyloxynonyloxy]pyrimidin-2-yl)benzyloxy]-1,4-dioxane.
40. The compound of claim 31 wherein said compound is trans-2,3-bis[4-(5-[10-acryloyloxydecyloxy]pyrimidin-2-yl)benzyloxy]-1,4-dioxane.
41. The compound of claim 31 wherein said compound is trans-2,3-bis[4-(5-[11-acryloyloxyundecyloxy]pyrimidin-2-yl)benzyloxy]-1,4-dioxane.
42. The compound of claim 31 wherein said compound is trans-2,3-bis[4-(5-[12-acryloyloxydodecyloxy]pyrimidin-2-yl)benzyloxy]-1,4-dioxane.
43. The compound of claim 30 wherein $D^1$ is 1,4-phenylene.
44. The compound of claim 43 wherein said compound is trans-2,3-bis(4-[3-acryloyloxypropyloxy]biphenyl-4'-methoxy)-1,4-dioxane.
45. The compound of claim 43 wherein said compound is trans-2,3-bis(4-[4-acryloyloxybutoxy]biphenyl-4'-methoxy)-1,4-dioxane.
46. The compound of claim 43 wherein said compound is trans-2,3-bis(4-[5-acryloyloxypentyloxy]biphenyl-4'-methoxy)-1,4-dioxane.
47. The compound of claim 43 wherein said compound is trans-2,3-bis(4-[6-acryloyloxyhexyloxy]biphenyl-4'-methoxy)-1,4-dioxane.
48. The compound of claim 43 wherein said compound is trans-2,3-bis(4-[7-acryloyloxyheptyloxy]biphenyl-4'-methoxy)-1,4-dioxane.
49. The compound of claim 43 wherein said compound is trans-2,3-bis(4-[8-acryloyloxyoctyloxy]biphenyl-4'-methoxy)-1,4-dioxane.
50. The compound of claim 43 wherein said compound is trans-2,3-bis(4-[9-acryloyloxynonyloxy]biphenyl-4'-methoxy)-1,4-dioxane.
51. The compound of claim 43 wherein said compound is trans-2,3-bis(4-[10-acryloyloxydecyloxy]biphenyl-4'-methoxy)-1,4-dioxane.
52. The compound of claim 43 wherein said compound is trans-2,3-bis(4-[11-acryloyloxyundecyloxy]biphenyl-4'-methoxy)-1,4-dioxane.
53. The compound of claim 43 wherein said compound is trans-2,3-bis(4-[12-acryloyloxydodecyloxy]biphenyl-4'-methoxy)-1,4-dioxane.
54. The compound of claim 30 wherein $D^1$ is pyridine-2,5-diyl.
55. The compound of claim 54 wherein said compound is trans-2,3-bis[4-(5-[3-acryloyloxypropyloxy]pyridin-2-yl)benzyloxy]-1,4-dioxane.
56. The compound of claim 54 wherein said compound is trans-2,3-bis[4-(5-[4-acryloyloxybutyloxy]pyridin-2-yl)benzyloxy]-1,4-dioxane.
57. The compound of claim 54 wherein said compound is trans-2,3-bis[4-(5-[5-acryloyloxypentyloxy]pyridin-2-yl)benzyloxy]-1,4-dioxane.
58. The compound of claim 54 wherein said compound is trans-2,3-bis[4-(5-[6-acryloyloxyhexyloxy]pyridin-2-yl)benzyloxy]-1,4-dioxane.
59. The compound of claim 54 wherein said compound is trans-2,3-bis[4-(5-[7-acryloyloxyheptyloxy]pyridin-2-yl)benzyloxy]-1,4-dioxane.
60. The compound of claim 54 wherein said compound is trans-2,3-bis[4-(5-[8-acryloyloxyoctyloxy]pyridin-2-yl)benzyloxy]-1,4-dioxane.
61. The compound of claim 54 wherein said compound is trans-2,3-bis[4-(5-[9-acryloyloxynonyloxy]pyridin-2-yl)benzyloxy]-1,4-dioxane.
62. The compound of claim 54 wherein said compound is trans-2,3-bis[4-(5-[10-acryloyloxydecyloxy]pyridin-2-yl)benzyloxy]-1,4-dioxane.
63. The compound of claim 54 wherein said compound is trans-2,3-bis[4-(5-[11-acryloyloxyundecyloxy]pyridin-2-yl)benzyloxy]-1,4-dioxane.
64. The compound of claim 54 wherein said compound is trans-2,3-bis[4-(5-[12-acryloyloxydodecyloxy]pyridin-2-yl)benzyloxy]-1,4-dioxane.
65. The compound of claim 54 wherein said compound is trans-2,3-bis[4-(5-[8-acryloyloxyoctyloxy]pyridin-2-yl)benzyloxy]-1,4-dioxane.
66. The compound of claim 29 wherein $C^1$ is pyrimidine-2,5-diyl.
67. The compound of claim 66 wherein said compound is trans-2,3-bis[[2-[4-(8-acryloyloxyoctyloxy)phenyl]pyrimidin-5-yl]methoxy]-1,4-dioxane.
68. The compound of claim 27 wherein $Z^{21}$ is —COO—.
69. The compound of claim 68 wherein $C^1$ is is pyridine-2,5-diyl, pyrimidine-2,5-diyl or 1,4-phenylene.
70. The compound of claim 69 wherein $C^1$ is 1,4-phenylene.

71. The compound of claim 70 wherein said compound is trans-2,3-Bis[4-(4-[3-acryloyloxypropyloxy]phenylcarbonyloxy)benzyloxy]-1,4-dioxane.

72. The compound of claim 70 wherein said compound is trans-2,3-bis[4-(4-[4-acryloyloxybutoxy]phenylcarbonyloxy)benzyloxy]-1,4-dioxane.

73. The compound of claim 70 wherein said compound is trans-2,3-bis[4-(4-[5-acryloyloxypentyloxy]phenylcarbonyloxy)benzyloxy]-1,4-dioxane.

74. The compound of claim 70 wherein said compound is trans-2,3-bis[4-(4-[6-acryloyloxyhexyloxy]phenylcarbonyloxy)benzyloxy]-1,4-dioxane.

75. The compound of claim 70 wherein said compound is trans-2,3-bis[4-(4-[7-acryloyloxyheptyloxy]phenylcarbonyloxy)benzyloxy]-1,4-dioxane.

76. The compound claim 70 wherein said compound is trans-2,3-bis[4-(4-[9-acryloyloxynonyloxy]phenylcarbonyloxy)benzyloxy]-1,4-dioxane.

77. The compound of claim 70 wherein said compound is trans-2,3-bis[4-(4-[10-acryloyloxydecyloxy]phenylcarbonyloxy)benzyloxy]-1,4-dioxane.

78. The compound of claim 70 wherein said compound is trans-2,3-bis[4-(4-[11-acryloyloxyundecyloxy]phenylcarbonyloxy)benzyloxy]-1,4-dioxane.

79. The compound of claim 70 wherein said compound is trans-2,3-bis[4-(4-[12-acryloyloxydodecyloxy]phenylcarbonyloxy)benzyloxy]-1,4-dioxane.

80. The compound of claim 20 having the formula:

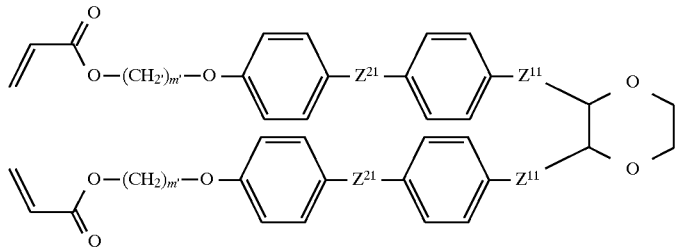

I-A wherein $Z^{11}$ is —COO—;

$Z^{21}$ is a single bond or —COO—; and m' is an integer from 3 to 12.

81. The compound of claim 80 wherein $Z^{21}$ is a single bond.

82. The compound of claim 81 wherein said compound is trans-2,3-bis(4-[3-acryloyloxypropyloxy]biphenyl-4'-carbonyloxy)-1,4-dioxane.

83. The compound of claim 81 wherein said compound is trans-2,3-bis(4-[4-acryloyloxybutoxy]biphenyl-4'-carbonyloxy)-1,4-dioxane.

84. The compound of claim 81 wherein said compound is trans-2,3-bis(4-[5-acryloyloxypentyloxy]biphenyl-4'-carbonyloxy)-1,4-dioxane.

85. The compound of claim 81 wherein said compound is trans-2,3-bis(4-[6-acryloyloxyhexyloxy]biphenyl-4'-carbonyloxy)-1,4-dioxane.

86. The compound of claim 81 wherein said compound is trans-2,3-bis(4-[7-acryloyloxyheptyloxy]biphenyl-4'-carbonyloxy)-1,4-dioxane.

87. The compound of claim 81 wherein said compound is trans-2,3-bis(4-[8-acryloyloxyoctyloxy]biphenyl-4'-carbonyloxy)-1,4-dioxane.

88. The compound of claim 81 wherein said compound is trans-2,3-bis(4-[9-acryloyloxynonyloxy]biphenyl-4'-carbonyloxy)-1,4-dioxane.

89. The compound of claim 81 wherein said compound is trans-2,3-bis(4-[10-acryloyloxydecyloxy]biphenyl-4'-carbonyloxy)-1,4-dioxane.

90. The compound of claim 81 wherein said compound is trans-2,3-bis(4-[11-acryloyloxyundecyloxy]biphenyl-4'-carbonyloxy)-1,4-dioxane.

91. The compound of claim 81 wherein said compound is trans-2,3-bis(4-[12-acryloyloxydodecyloxy]biphenyl-4'-carbonyloxy)-1,4-dioxane.

92. The compound of claim 81 wherein $Z^{21}$ is —COO—.

93. The compound of claim 92 wherein said compound is trans-2,3-bis[4-(4-[8-acryloyloxyoctyloxy]phenylcarbonyloxy)phenylcarbonyloxy]-1,4-dioxane.

94. The compound of claim 92 wherein said compound is trans-2,3-Bis[4-(4-[3-acryloyloxypropyloxy]phenylcarbonyloxy)-phenylcarbonyloxy]-1,4-dioxane.

95. The compound of claim 92 wherein said compound is trans-2,3-bis[4-(4-[4-acryloyloxybutoxy]phenylcarbonyloxy)phenyl-carbonyloxy]-1,4-dioxane.

96. The compound of claim 92 wherein said compound is trans-2,3-bis[4-(4-[5-acryloyloxypentyloxy]phenylcarbonyloxy)phenylcarbonyloxy]-1,4-dioxane.

97. The compound of claim 92 wherein said compound is trans-2,3-bis[4-(4-[6-acryloyloxyhexyloxy]phenylcarbonyloxy)phenylcarbonyloxy]-1,4-dioxane.

98. The compound of claim 92 wherein said compound is trans-2,3-bis[4-(4-[7-acryloyloxyheptyloxy]phenylcarbonyloxy)-phenylcarbonyloxy]-1,4-dioxane.

99. The compound of claim 92 wherein said compound is trans-2,3-bis[4-(4-[9-acryloyloxynonyloxy]phenylcarbonyloxy)phenylcarbonyloxy]-1,4-dioxane.

100. The compound of claim 92 wherein said compound is trans-2,3-bis[4-(4-[10-acryloyloxydecyloxy]phenylcarbonyloxy)phenylcarbonyloxy]-1,4-dioxane.

101. The compound of claim 92 wherein said compound is trans-2,3-bis[4-(4-[11-acryloyloxyundecyloxy]phenylcarbonyloxy)phenylcarbonyloxy]-1,4-dioxane.

102. The compound of claim 92 wherein said compound is trans-2,3-bis[4-(4-[12-acryloyloxydodecyloxy]phenylcarbonyloxy)phenylcarbonyloxy]-1,4-dioxane.

103. The compound of claim 20 having the formula:

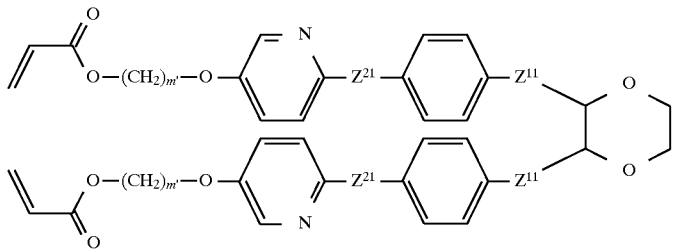

wherein $Z^{11}$ is —COO—;

$Z^{21}$ is a single bond or —COO—, and m is an integer from 3 to 12.

104. The compound of claim 103 wherein $Z^{21}$ is a single bond.

105. The compound of claim 104 wherein said compound is trans-2,3-bis[4-(5-[3-acryloyloxypropyloxy]pyridin-2-yl)phenyl-carbonyloxy]-1,4-dioxane.

106. The compound of claim 104 wherein said compound is trans-2,3-bis[4-(5-[4-acryloyloxybutyloxy]pyridin-2-yl)phenylcarbonyloxy]-1,4-dioxane.

107. The compound of claim 104 wherein said compound is trans-2,3-bis[4-(5-[5-acryloyloxypentyloxy]pyridin-2-yl)phenylcarbonyloxy]-1,4-dioxane.

108. The compound of claim 104 wherein said compound is trans-2,3-bis[4-(5-[6-acryloyloxyhexyloxy]pyridin-2-yl phenylcarbonyloxy]-1,4-dioxane.

109. The compound of claim 104 wherein said compound is trans-2,3-bis[4-(5-[7-acryloyloxyheptyloxy]pyridin-2-yl)phenylcarbonyloxy]-1,4-dioxane.

110. The compound of claim 104 wherein said compound is trans-2,3-bis[4-(5-[8-acryloyloxyoctyloxy]pyridin-2-yl)phenylcarbonyloxy]-1,4-dioxane.

111. The compound of claim 104 wherein said compound is trans-2,3-bis[4-(5-[9-acryloyloxynonyloxy]pyridin-2-yl)phenylcarbonyloxy]-1,4-dioxane.

112. The compound of claim 104 wherein said compound is trans-2,3-bis[4-(5-[10-acryloyloxydecyloxy]pyridin-2-yl)phenylcarbonyloxy]-1,4-dioxane.

113. The compound of claim 104 wherein said compound is trans-2,3-bis[4-(5-[11-acryloyloxyundecyloxy]pyridin-2-yl)phenylcarbonyloxy]-1,4-dioxane.

114. The compound of claim 104 wherein said compound is trans-2,3-bis[4-(5-[12-acryloyloxydodecyloxy]pyridin-2-yl)phenylcarbonyloxy]-1,4-dioxane.

115. The compound of claim 103 wherein $Z^{21}$ is —COO—.

116. The compound of claim 20 having the formula:

wherein $Z^{11}$ is —COO—;

$Z^{21}$ is a single bond or —COO—, especially —COO—; and m' is a whole number of 3 to 12.

117. The compound of claim 116 wherein $Z^{21}$ is a single bond.

118. The compound of claim 117 wherein said compound is trans-2,3-bis[4-(5-[3-acryloyloxypropyloxy]pyrimidin-2-yl)phenyl-carbonyloxy]-1,4-dioxane.

119. The compound of claim 117 wherein said compound is trans-2,3-bis[4-(5-[4-acryloyloxybutyloxy]pyrimidin-2-yl)phenyl-carbonyloxy]-1,4-dioxane.

120. The compound of claim 117 wherein said compound is trans-2,3-bis[4-(5-[5-acryloyloxypentyloxy]pyrimidin-2-yl)phenylcarbonyloxy]-1,4-dioxane.

121. The compound of claim 117 wherein said compound is trans-2,3-bis[4-(5-[6-acryloyloxyhexyloxy]pyrimidin-2-yl)phenylcarbonyloxy]-1,4-dioxane.

122. The compound of claim 117 wherein said compound is trans-2,3-bis[4-(5-[7-acryloyloxyheptyloxy]pyrimidin-2-yl)phenylcarbonyloxy]-1,4-dioxane.

123. The compound of claim 117 wherein said compound is trans-2,3-bis[4-(5-[8-acryloyloxyoctyloxy]pyrimidin-2-yl)phenylcarbonyloxy]-1,4-dioxane.

124. The compound of claim 117 wherein said compound is trans-2,3-bis[4-(5-[9-acryloyloxynonyloxy]pyrimidin-2-yl)phenylcarbonyloxy]-1,4-dioxane.

125. The compound of claim 117 wherein said compound is trans-2,3-bis[4-(5-[10-acryloyloxydecyloxy]pyrimidin-2-yl)phenylcarbonyloxy]-1,4-dioxane.

126. The compound of claim 117 wherein said compound is trans-2,3-bis[4-(5-[11-acryloyloxyundecyloxy]pyrimidin-2-yl)phenylcarbonyloxy]-1,4-dioxane.

127. The compound of claim 117 wherein said compound is trans-2,3-bis[4-(5-[12-acryloyloxydodecyloxy]pyrimidin-2-yl)phenylcarbonyloxy]-1,4-dioxane.

128. The compound of claim 116 wherein $Z^{21}$ is —COO—.

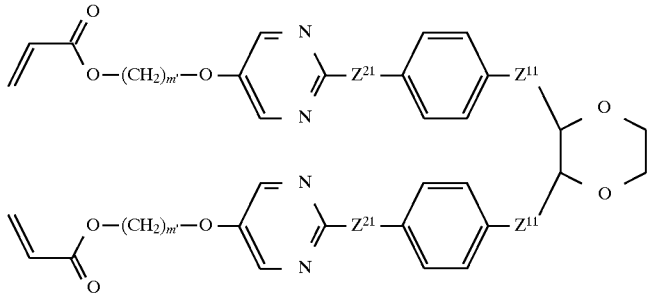

129. A cross-linkable, liquid crystalline mixture comprising a, compound of claim 1 and a second liquid crystalline compound having a photo crosslinkable group.
130. The cross-linkable, liquid crystalline mixture of claim 129 wherein said second compound is a compound of the formula:
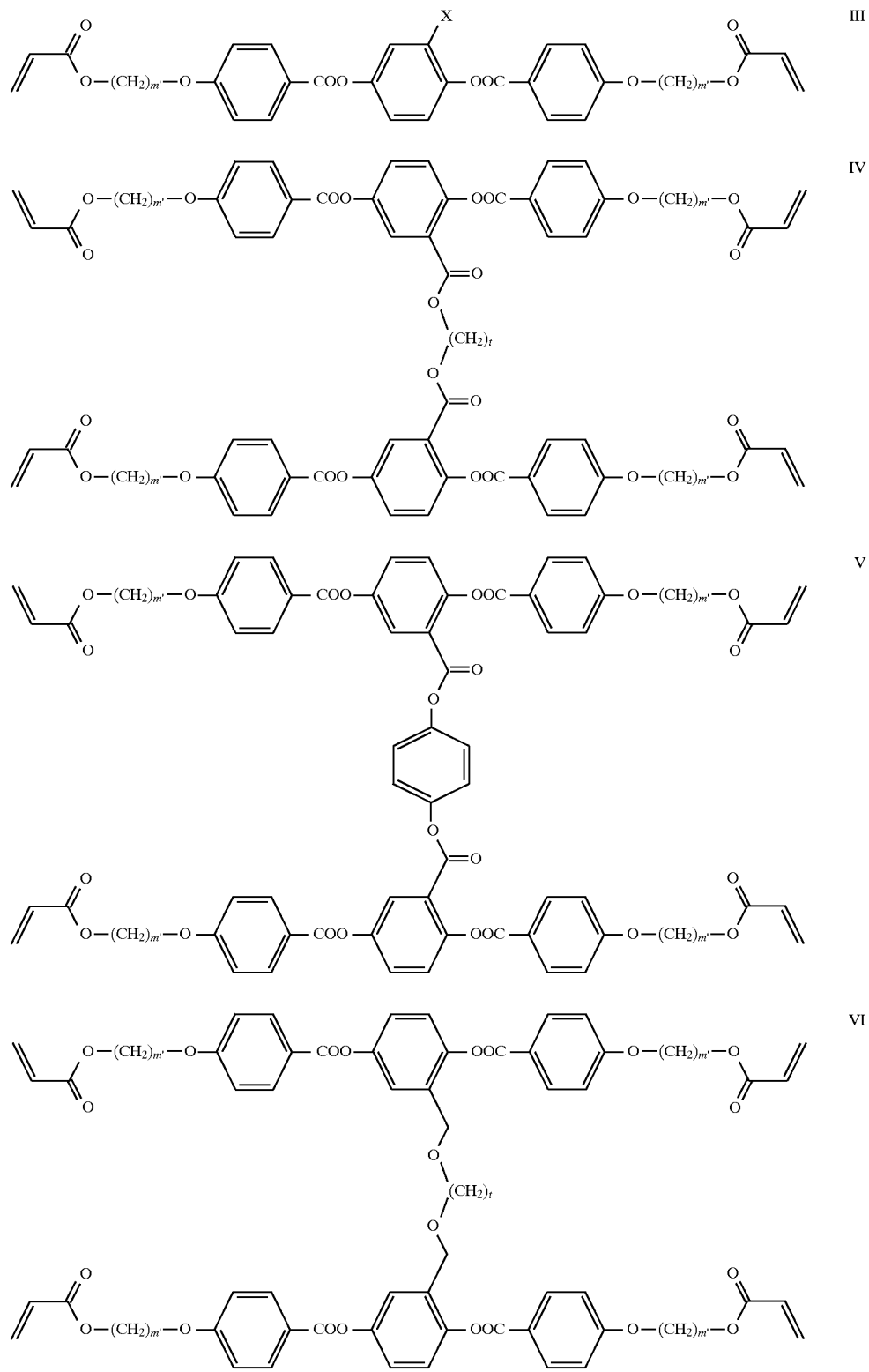

-continued
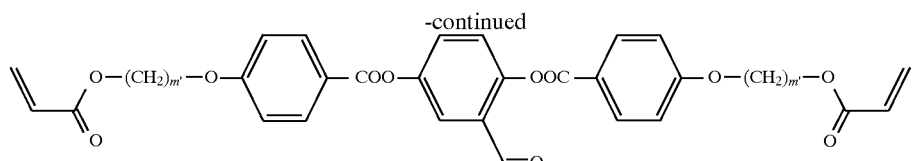
VII
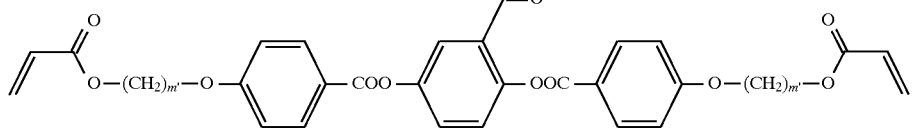
VIII
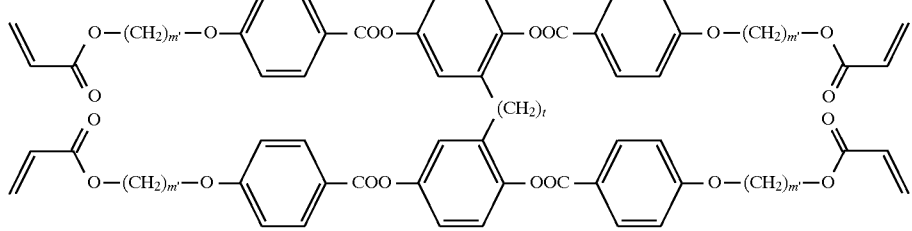
IX
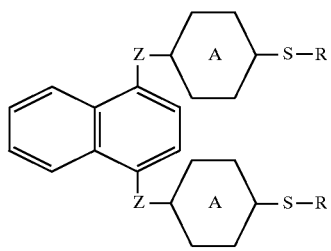
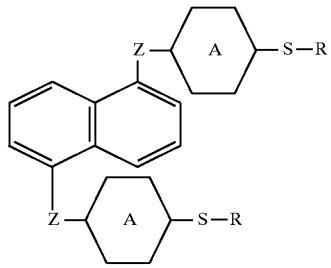
X
wherein
X is hydrogen, fluorine, chlorine, bromine or methyl;
m' is an integer from 3 to 12;
t is an integer from 2 to 12;
Z is —OCH$_2$— or —OOC—;
A is 1,4-phenylene or 2- or 3-fluoro-1,4-phenylene;
S is —(CH$_2$)$_{m'}$— or —(CH$_2$)$_{m'}$O—; and
R is CH$_2$=CH—COO—, CH$_2$=C(CH$_3$)—COO—, CH$_2$=CH—O— or
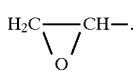
* * * * *